(12) United States Patent
Misner et al.

(10) Patent No.: US 8,555,901 B2
(45) Date of Patent: Oct. 15, 2013

(54) DENTAL FLOSSER

(75) Inventors: Chad Misner, Arlington Heights, IL (US); Leoncio Angel Gonzalez, Winfield, IL (US); Russell G. Kalbfeld, Naperville, IL (US)

(73) Assignee: Sunstar Americas, Inc., Chicago, IL (US)

( * ) Notice: Subject to any disclaimer, the term of this patent is extended or adjusted under 35 U.S.C. 154(b) by 327 days.

(21) Appl. No.: 12/696,714

(22) Filed: Jan. 29, 2010

(65) Prior Publication Data

US 2011/0186074 A1    Aug. 4, 2011

(51) Int. Cl.
*A61C 15/00* (2006.01)

(52) U.S. Cl.
USPC .......................................................... 132/323

(58) Field of Classification Search
USPC ............... 132/322–329; D28/65, 66
See application file for complete search history.

(56) References Cited

U.S. PATENT DOCUMENTS

| | | |
|---|---|---|
| D284,896 S | 7/1986 | Ching-Chou |
| D301,071 S | 5/1989 | Franchi |
| D316,617 S | 4/1991 | Cheung |
| D348,332 S | 6/1994 | Haggett-King et al. |
| 5,388,600 A | 2/1995 | Hart |
| 5,738,125 A | 4/1998 | Lin |
| D412,043 S | 7/1999 | Dolan et al. |
| D424,748 S | 5/2000 | Dolan et al. |
| 6,065,479 A | 5/2000 | Chodorow |
| D521,189 S | 5/2006 | Winkler et al. |
| D531,758 S | 11/2006 | Jansheski et al. |
| D532,160 S | 11/2006 | Jansheski et al. |
| 7,171,971 B2 | 2/2007 | Ochs et al. |
| 7,234,475 B2 | 6/2007 | Ding et al. |
| D560,442 S | 1/2008 | Teys et al. |
| D607,606 S | 1/2010 | Chodorow et al. |
| D609,405 S | 2/2010 | Jansheski et al. |
| D624,703 S | 9/2010 | Misner et al. |
| 2003/0150474 A1* | 8/2003 | Doyscher ...................... 132/325 |
| 2005/0133058 A1 | 6/2005 | Ding |

OTHER PUBLICATIONS

International Search Report and Written Opinion of the International Searching Authority, International Patent Application No. PCT/US2011/022708, mailed Mar. 17, 2011.
PCT/US2011/022708 International Preliminary Report on Patentability dated Jul. 31, 2012 (6 pages).

* cited by examiner

*Primary Examiner* — Rachel Steitz
(74) *Attorney, Agent, or Firm* — Michael Best & Friedrich LLP

(57) ABSTRACT

An oral care device having a handle, a neck, and a pair of curved arms. The handle includes an enlarged distal end and a reduced proximal end, and a pair of downwardly-extending handle walls. The handle walls are spaced at their upper ends and converge with and join one another at their lower ends to define a substantially V-shaped cross-section and an upwardly-opening blind cavity. A neck extends distally from the handle and defines a tongue portion that is recessed relative to a top surface. A pair of curved arms extend distally and downwardly from the neck. When substantially identical oral care devices are stacked one upon the other, the upwardly-opening blind cavity of one oral care device nestingly receives the downwardly-extending handle walls of another oral care device.

16 Claims, 6 Drawing Sheets

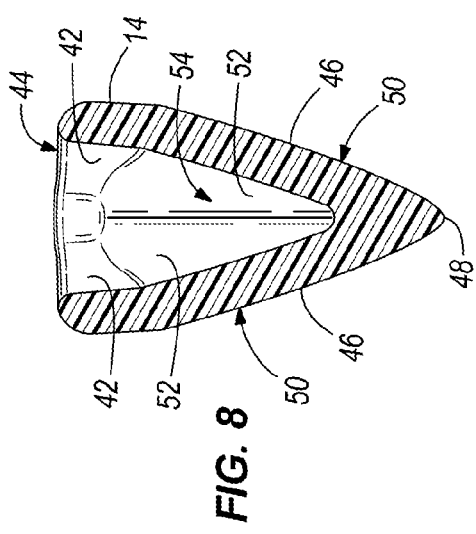
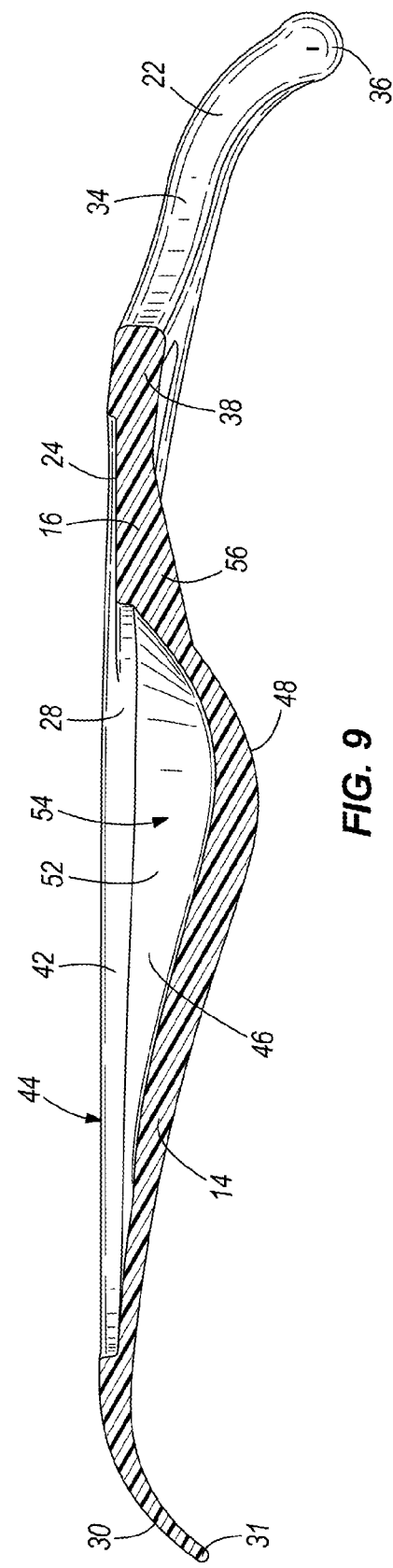

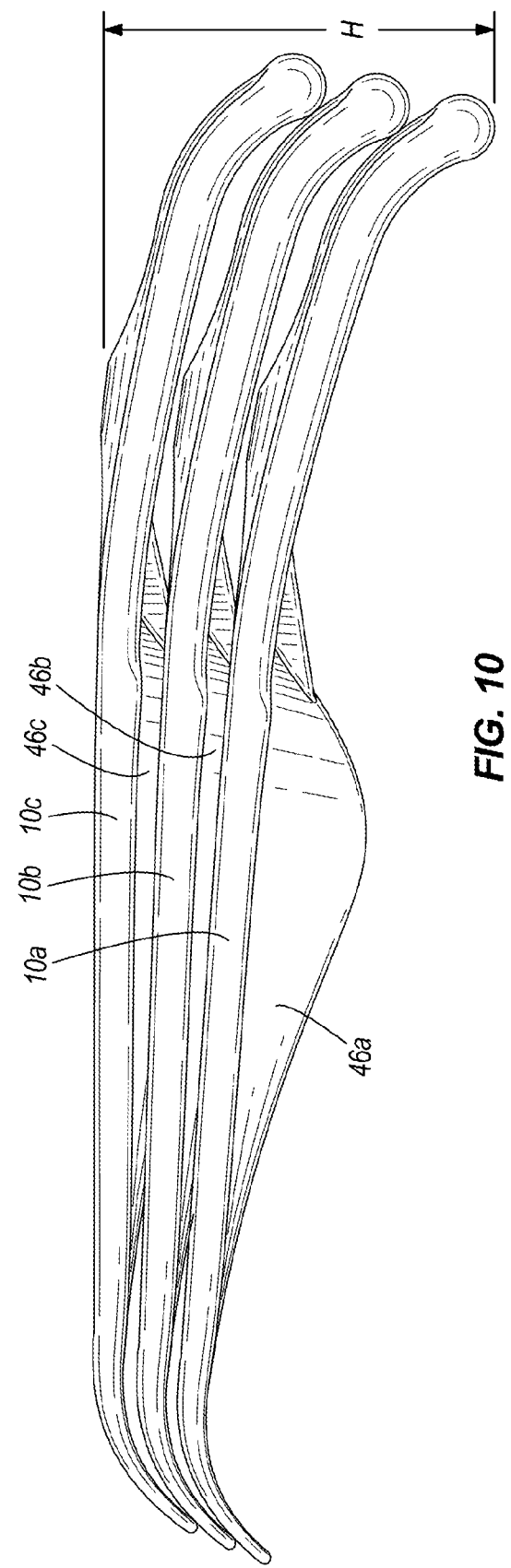

DENTAL FLOSSER

BACKGROUND

The present invention relates to dental flossers.

Daily flossing is a fundamental part of a person's complete oral hygiene program. Brushing and cleaning one's teeth without flossing leaves a large portion of the tooth surfaces uncleaned. Flossing helps to remove harmful plaque and bacteria from between person's teeth, where a toothbrush cannot reach. It is well known that plaque build-up can lead to gum disease, chronic bad breath, tooth loss and other ailments.

Dental flossing devices are known for simplifying the flossing process for certain users. Reusable flossers generally include a handle, a pair of spaced apart arms, and a floss retention device. A length of floss is connected to the floss retention device and the floss is strung between the spaced apart arms. A user can then floss using the handle to manipulate the portion of the floss between the arms into the spaces between his or her teeth. When the user is finished using flossing, the floss it is removed and discarded. Subsequent uses require a new length of floss to be connected to the floss retention device.

Disposable flossers that are packaged and sold in large quantities are also known. Disposable flossers are generally formed of an inexpensive plastic material and also include a handle, a pair of spaced apart arms, and a length of floss connected to, and extending between, the arms. Disposable flossers are preferred by some users because of their low cost and convenience. In most disposable flossers, the length of floss extending between the arms is integrally molded with the flosser body during manufacturing and cannot be replaced. Disposable flossers are generally discarded after a single use.

SUMMARY

In some constructions, an oral care device is provided having a handle and a pair of curved arms. The handle includes a converging pair of handle walls that cooperate to define a cavity. The pair of curved arms are connected to the handle and include distal ends. A length of thread is coupled to and extends between the distal ends of the arms. When substantially identical oral care devices are stacked one upon the other, the cavity of one oral care device receives the converging pair of handle walls of the other oral care device in a nested manner.

In another construction, an oral care device is provided that includes a handle having a pair of downwardly-extending handle walls. The handle walls are spaced from one another at their upper ends and converge with and join one another at their lower ends to define a substantially V-shaped handle cross-section. The handle also defines an upwardly-opening blind cavity. The oral care device further includes a neck portion extending from the distal end of the handle, and a pair of downwardly-curving arms extending distally from the neck portion. A length of thread is coupled to and extends between the distal ends of the arms. When substantially identical oral care devices are stacked one upon the other, the upwardly-opening blind cavity of one oral care device nestingly receives the downwardly-extending handle walls of another oral care device.

In further embodiments, an oral care device is provided that includes a handle having an enlarged distal end and a reduced proximal end, the handle tapering from the distal end to the proximal end. The handle includes a pair of downwardly-extending handle walls. The handle walls are spaced from one another at their upper ends and are converging with and joining one another at their lower ends to define a substantially V-shaped cross-section. The handle also defines an upwardly-opening blind cavity. The oral care device further includes a neck extending distally from the distal end of the handle, the neck defining a neck portion of the device's top surface and a tongue portion that is recessed relative to the device top surface and substantially adjacent the handle. The oral care device also includes a pair of curved arms extending distally and downwardly from the neck, the arms defining a convex arm portion of the device top surface and converging toward one another such that distal ends of the arms are closer to one another than proximal ends of the arms. A length of thread is coupled to and extends between the distal ends of the arms. When substantially identical oral care devices are stacked one upon the other, the upwardly-opening blind cavity of one oral care device nestingly receives the downwardly-extending handle walls of another oral care device.

Other aspects of the invention will become apparent by consideration of the detailed description and accompanying drawings.

BRIEF DESCRIPTION OF THE DRAWINGS

FIG. 8 is a section view taken along line 8-8 in FIG. 4.

FIG. 9 is a section view taken along line 9-9 in FIG. 2.

FIG. 10 is a side view of three nested flossers.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Figure 1:
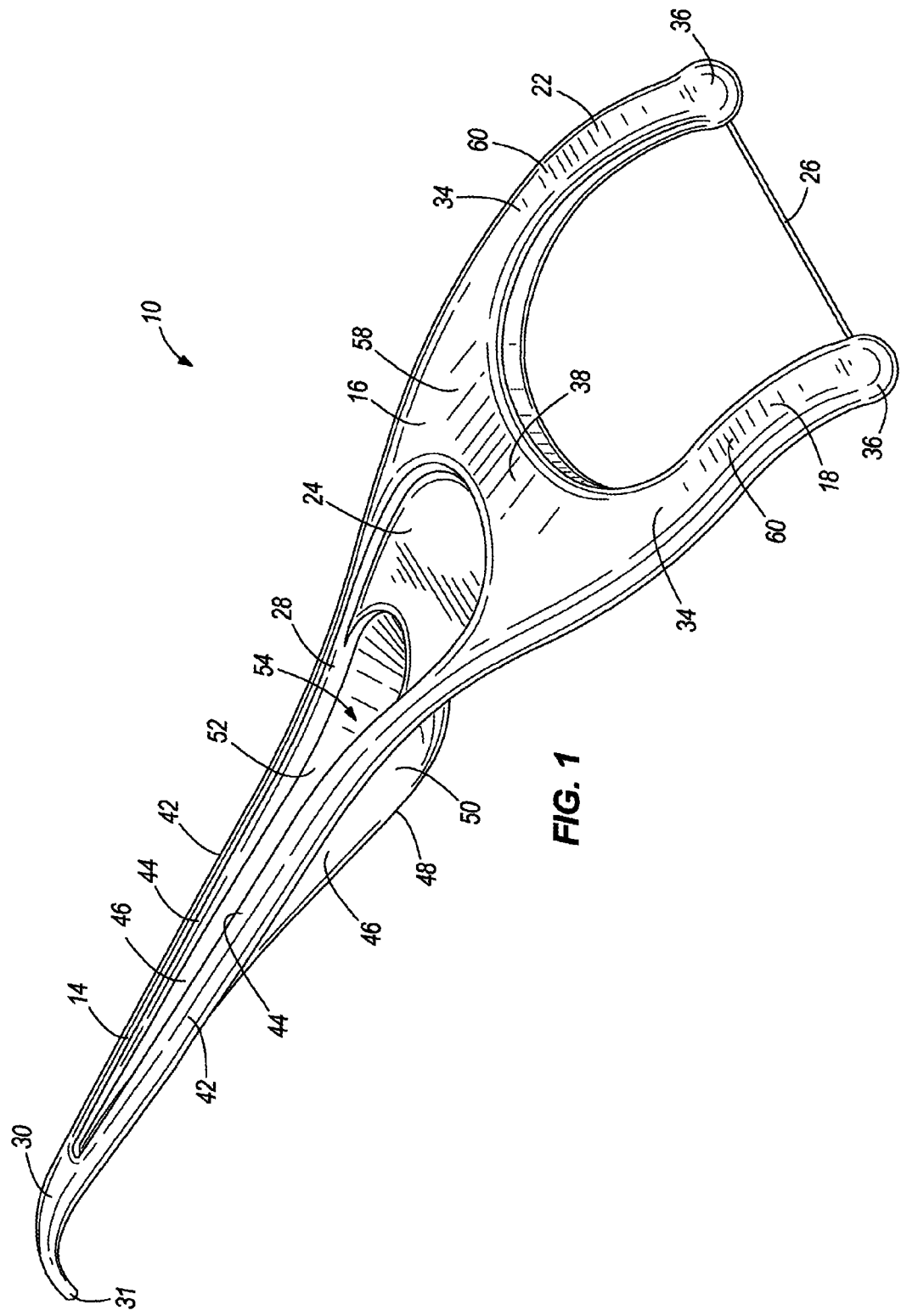
FIG. 1 is a perspective view of a dental flosser embodying the invention.
Figure 2:
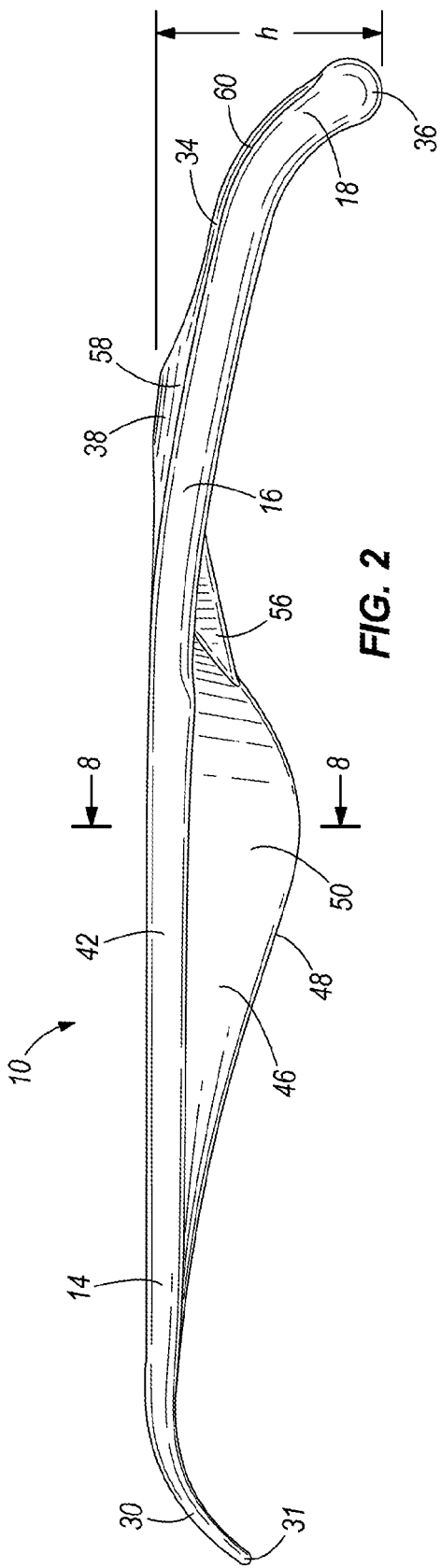
FIG. 2 is a right side view of the dental flosser of FIG. 1.
Figure 3:
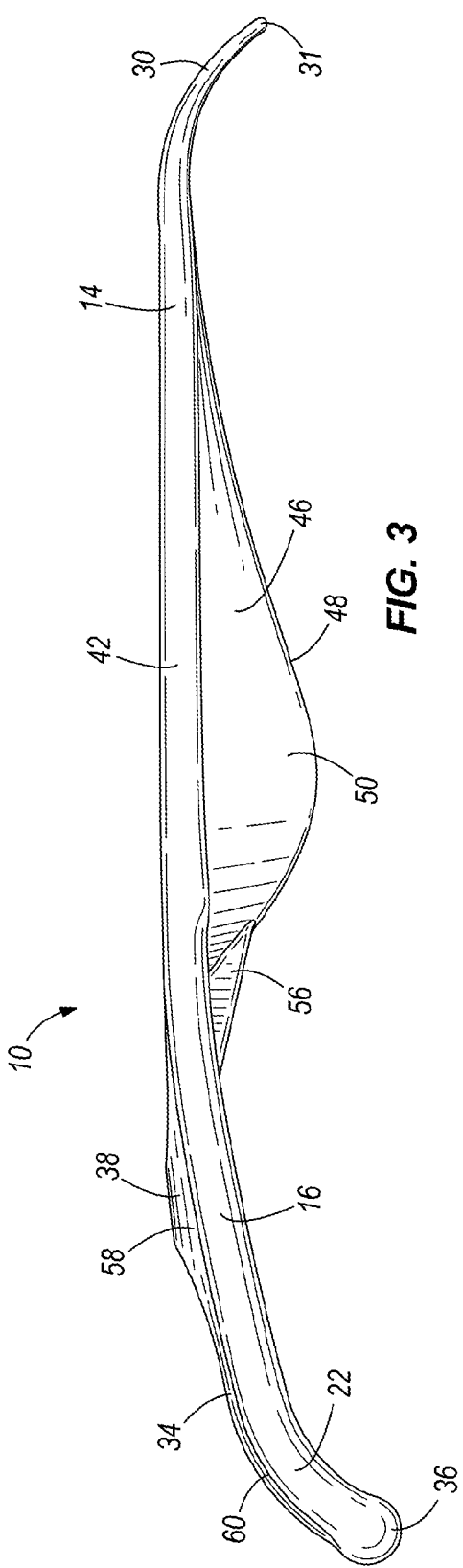
FIG. 3 is a left side view of the dental flosser of FIG. 1.
Figure 4:
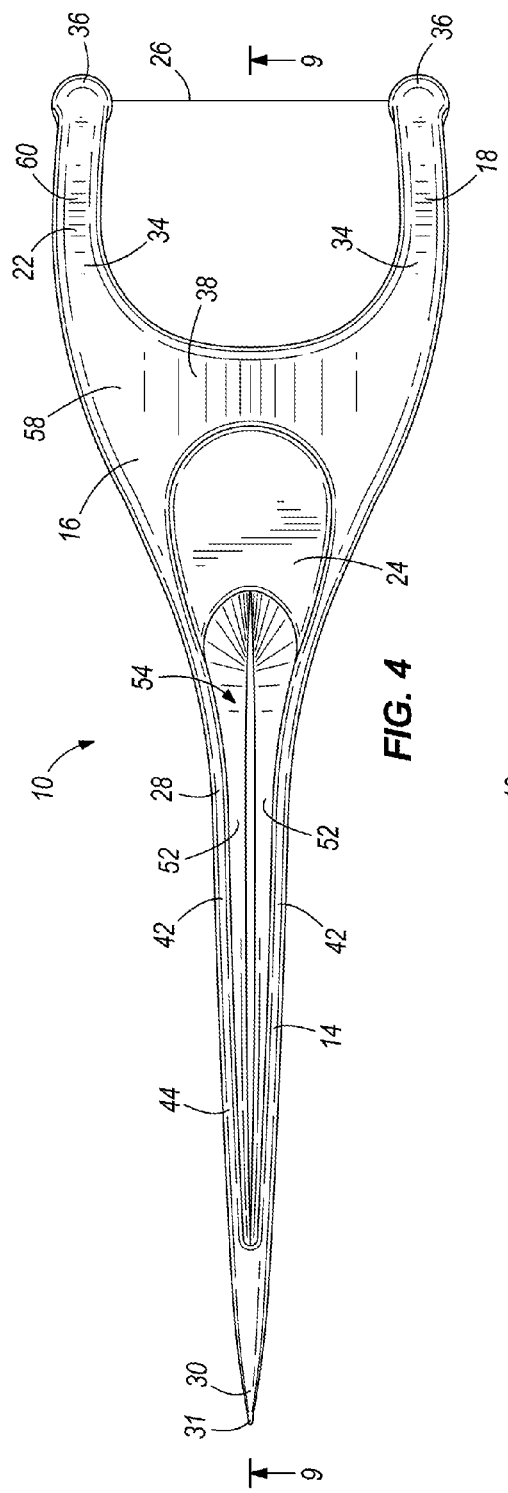
FIG. 4 is a top view of the dental flosser of FIG. 1.

FIG. 1 illustrates an oral care device in the form of a dental flosser 10 embodying the invention. The flosser 10 includes a handle 14 that allows a user to hold and manipulate the flosser 10, a neck 16 extending distally from the handle and also allowing the user to hold and manipulate the flosser 10, and a pair of curved and spaced-apart arms 18, 22 extending distally from the neck 16 and adapted for positioning on opposing sides of the user's teeth. The flosser 10 also includes a length of thread in the form of dental floss 26 extending between the arms 18, 22 for insertion into the spaces between the user's teeth. The floss 26 is firmly connected to the arms 18 and 22 to allow a user to insert the floss into the space between his or her teeth in order to clean the plaque and other debris from the teeth.

Referring also to FIGS. 2-7, the handle 14 includes an enlarged distal end 28 and a reduced proximal end 30. The handle 14 tapers gradually from the distal end 28 to the proximal end 30, and includes on the proximal end 30 a curved dental pick 31 that, like the floss 26, may be used for cleaning debris from the teeth. The handle 14 includes a pair of elongated and substantially opposed rail-like side portions 42 that extend between the distal end 28 and the proximal end 30. Each side portion 42 defines a handle top surface 44. The handle 14 also includes a pair of downwardly extending handle walls 46. Each handle wall 46 extends downwardly from a respective one of the side portions 42 and converges toward the other of the handle walls 46. The handle walls 46 converge to define a curved bottom edge 48 that, when viewed from the side, extends generally downardly and at a relatively steep angle from a location near the distal end 28, and then curves gradually upwardly at a shallower angle toward the handle 14 proximal end 30 (see FIGS. 2 and 3).

With reference also to FIGS. 8 and 9, the handle walls 46 are spaced from one another at their upper ends and converge with and join one another at their lower ends to define a substantially V-shaped handle cross-section (FIG. 8). Each handle wall 46 includes an outer surface 50 and an inner surface 52. The outer surfaces 50 are angled relative to one another and are appropriately located and configured such that, during use, one of the outer surfaces may be grasped by the thumb of a user, and the other of the outer surfaces 50 may be grasped by the middle finger of a user. The inner surfaces 52 of the handle walls 46 cooperate to define an upwardly-opening blind cavity 54. The blind cavity 54 extends between the side portions 42 from the distal end 28 to the proximal end 30 of the handle 14, and is recessed relative to the handle top surface 44. In this way, the side portions 42 generally define the opening of the blind cavity 54.

The neck 16 extends distally from the distal end 28 of the handle 14. When viewed from above or below, the neck 16 gradually widens to define an arm support portion 38 as the neck 16 extends away from the distal end 28 of the handle 14 (see FIGS. 4 and 5). The neck 16 defines a generally convex neck top surface 58 and a tongue portion 24 that is recessed relative to the neck top surface 58 and located adjacent to the handle 14. The recessed tongue portion 24 opens into and extends distally from a distal portion of the blind cavity 54. The tongue portion 24 is positioned in an appropriate location for receiving the index finger of a user. The recessed nature of the tongue portion 24 affords the user greater control during manipulation of the flosser 10 within the user's mouth. Furthermore, in combination with the angled outer surfaces 50 of the handle walls 46, which as mentioned above are appropriately located and configured for receiving the thumb and middle finger of a user, the user is provided with three complimentary points of contact for manipulating the flosser 10.

Figure 5:
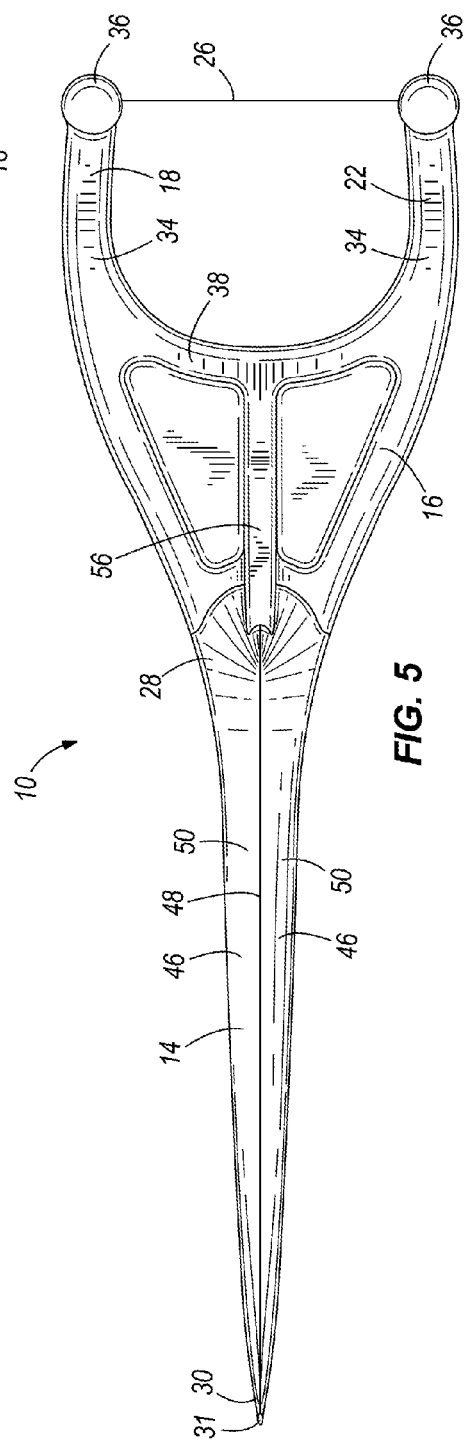
FIG. 5 is a bottom view of the dental flosser of FIG. 1.
Figure 6:
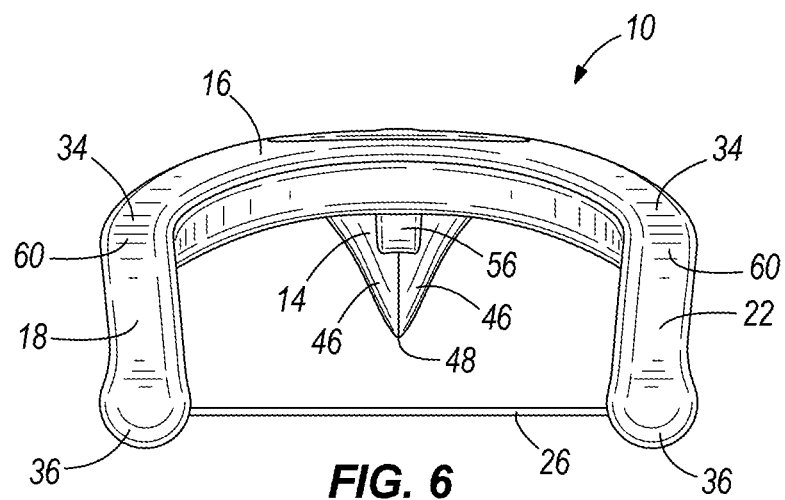
FIG. 6 is a front view of the dental flosser of FIG. 1.
Figure 7:
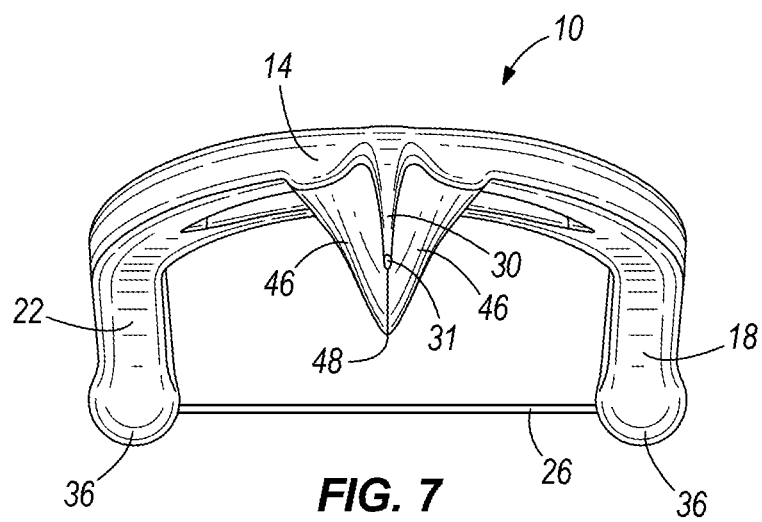
FIG. 7 is a rear view of the dental flosser of FIG. 1.

As shown in FIGS. 5 and 9, the underside of the neck 16 includes a rib portion 56 oriented generally perpendicular to the neck 16 and extending between the handle walls 46 and an underside of the neck 16. In the illustrated construction, the rib portion 56 includes a single rim extending from the support portion 38 of the neck 16 rearwardly and downwardly toward the curved bottom edge 48 defined by the handle walls 46. The rib portion 56 provides additional structural integrity to the flosser by resisting bending of the flosser 10 about the otherwise relatively thin portion of the neck 16 in the vicinity of the tongue portion 24 (see FIG. 9). In this way, the rib portion 56 allows a user to apply greater force to the flosser 10 when manipulating the floss 26 into the spaces between the user's teeth.

The arms 18 and 22 extend distally and curve downwardly from the support portion 38 of the neck 16. The arms 18 and 22 together define a convex arm top surface 60 that, in the illustrated construction, is substantially continuous with the neck top surface 58. The arms 18 and 22 have arm proximal ends 34 and arm distal ends 36. The arms 18 and 22 converge toward one another in the distal direction such that the arm distal ends 36 are closer to one another than the arm proximal ends 34 (see FIGS. 4-7). The arm distal ends 36 are substantially ball-shaped to improve user comfort when the arm distal ends 36 contact the soft tissues of the cheek and gums during use. In some constructions, the arm distal ends 36 are molded over the floss 26 in a known manner such that the floss 26 is securely held between the arm distal ends 36.

In one possible method of use, a user grasps the handle 14 of the flosser 10 and places his or her index finger into the recessed tongue portion 24 and his or her thumb and middle finger on opposing ones of the handle walls 46. The user then positions at least the arms 18, 22 into his or her mouth. The user then aligns the floss 26 with the space between a pair of adjacent teeth, and, by applying downward pressure to the recessed tongue portion 24 using the index finger, urges the floss 26 through the crown area of the adjacent teeth and into the interdental space adjacent the gum line. The user then manipulates the tongue portion 24 and opposing handle walls 46 to maneuver the floss 26 into contact with the teeth and gums surrounding the interdental space, thereby removing plaque and other debris from the teeth and gums. The user may then remove the flosser 10 from the interdental space by applying upward pressure against the opposing handle walls 46 using the thumb and middle finger. Thereafter, the process may be repeated on other interdental spaces. It should be appreciated that users may grasp and manipulate the flosser in different ways using different combinations of the thumb and fingers; however, it should be appreciated the combination of the tongue portion 24 and the V-shaped handle walls 46 allow the user to apply forces in opposite directions (e.g., upwardly and downwardly) without having to adjust the grip upon the flosser 10.

With reference to FIG. 10, the flosser 10 is constructed such that a plurality of the flossers 10 may be stacked, one upon the other, in a nested manner, in which a projecting portion of one of the flossers 10 fits within a complimentarily recessed portion of another of the flossers 10. As a result, a stacked height "H" of a plurality of stacked flossers is less than a height "h" of an individual flosser 10 (see FIG. 2) multiplied by the number of flossers in the stack. To provide this nesting configuration, the blind cavity 54 and handle walls 46 of the flosser 10 are configured to receive and be received by, respectively, the handle walls 46 and blind cavity 54 of another flosser. FIG. 10 illustrates a bottom flosser 10a, a middle flosser 10b, and a top flosser 10c, each of the flossers, 10a, 10b, and 10c, being substantially identical with the others. As shown, the handle walls 46c of the top flosser 10c are received within the blind cavity 54 (not labeled in FIG. 10) of the flosser 10b. In turn, the handle walls 46b of the middle flosser 10b are received within the blind cavity 54 (not labeled in FIG. 10) of the flosser 10a. In this arrangement, the outer surfaces 50 (not labeled in FIG. 10) of the handle walls 46c and 46b face and nest between the inner surfaces 52 (not labeled in FIG. 10) of the handle walls 46b and 46a, respectively.

Also, as shown in FIG. 8, the blind cavity is shaped in a manner that is complimentary to the shape of the bottom edge 48. Furthermore, the downward curvature of the arms 18, 22 is such that the arm distal ends 36 of an upper flosser (e.g., the flosser 10c in FIG. 10) engage the arm top surface 60 of a lower flosser (e.g., the flosser 10b in FIG. 10). These complimentary features provide multiple points of contact that allow the flossers to nest together in a manner that results in a relatively stable stack of flossers 10. Once stacked, the flossers 10 generally can be moved and manipulated as a stack, in some embodiments this features affords enhanced manufacturing efficiency. The nesting engagement between flossers 10 also allows the flossers 10 to be stacked more compactly, securely, and neatly within a packaging container when compared to conventional, non-nesting flossers. In this way, the amount of packaging required for a given number of flossers may be reduced, thereby reducing overall costs for the flosser manufacturing and packaging operation.

What is claimed is:

1. An oral care device comprising:
    a handle including a top surface, a bottom surface, and a pair of intersecting handle walls, the handle walls forming a cavity in the top surface;
    a pair of arms connected to the handle at a first end of the handle, the arms being curved downwards away from the top surface; and
    a length of thread coupled to and extending between distal ends of the arms,
    wherein the handle walls form a portion in the bottom surface of the handle which is configured to be received by the cavity in the top surface of a substantially identical oral care device so that the oral care devices are nestable when a plurality of the oral care devices are stacked one upon the other.

2. The oral care device of claim 1, wherein the handle includes a second end, and a pair of substantially opposed side portions extending between the first end and the second end and defining an opening of the cavity.

3. The oral care device of claim 2, wherein each handle wall extends generally downwardly and inwardly from a respective one of the side portions and converges toward and with the other handle wall to define a curved bottom surface that extends between the first end and the second end of the handle.

4. The oral care device of claim 2, wherein each handle wall includes an outer surface and an inner surface, the inner surfaces of the handle walls forming the cavity, the cavity being blind and extending generally from the first end to the second end of the handle.

5. The oral care device of claim 2, wherein the second end has a substantially pointed shape.

6. The oral care device of claim 1, further comprising a neck connecting the handle and the arms, and a rib portion oriented generally perpendicular to the neck and extending between the handle walls and an underside of the neck.

7. The oral care device of claim 6, wherein the neck includes a recessed tongue portion that opens into and extends from an end of the cavity.

8. An oral care device comprising:
    a handle including a top surface and a pair of handle walls extending downwardly from the top surface, the handle walls spaced from one another at upper ends thereof and intersecting one another at lower ends thereof to define a substantially V-shaped handle cross-section, the handle walls forming an upwardly-opening blind cavity in the top surface;
    a neck portion extending from a first end of the handle;
    a pair of arms connected to the neck portion at the first end of the handle, the arms being curved downwards away from the top surface; and
    a length of thread coupled to and extending between distal ends of the arms;
    wherein the handle walls form a portion in a bottom surface of the handle which is configured to be received by the cavity in the top surface of a substantially identical, oral care device so that the oral care devices are nestable when a plurality of the oral care devices are stacked one upon the other.

9. The oral care device of claim 8, wherein the arms converge toward one another such that the distal ends of the arms are closer to one another than proximal ends of the arms.

10. The oral care device of claim 8, wherein the handle includes an enlarged first end, a reduced second end, and a pair of side portions extending between the first end and the second end and forming the opening of the blind cavity.

11. The oral care device of claim 10, wherein each handle wall extends downwardly and inwardly from a respective one of the side portions and converges toward and with the other handle wall to define a curved bottom surface that extends between the first end and the second end of the handle.

12. The oral care device of claim 10, wherein the second end has a substantially pointed shape.

13. The oral care device of claim 8, wherein the neck portion includes a recessed tongue portion that opens into and extends distally from an end of the cavity.

14. The oral care device of claim 8, further comprising a rib portion oriented generally perpendicular to the neck portion and extending between the handle walls and an underside of the neck portion.

15. The oral care device of claim 8, wherein a number of oral care devices are arranged in a stack, and wherein a stacked height of the stack is less than a height of an individual oral care device multiplied by the number of oral care devices in the stack.

16. An oral care device comprising:
    a handle including an enlarged first end and a reduced second end, the handle tapering from the first end to the second end, a top surface, and a pair of handle walls extending downwardly from the top surface, the handle walls spaced from one another at upper ends thereof and intersecting one another at lower ends thereof to define a substantially V-shaped cross-section, the handle forming an upwardly-opening blind cavity in the top surface;
    a neck extending from the first end of the handle, the neck defining a neck portion of the handle top surface and a tongue portion that is recessed relative to the top surface and substantially adjacent the handle;
    a pair of arms curving downwardly from the neck, the arms defining a convex arm portion of the device top surface and converging toward one another such that ends of the arms opposite the handle are closer to one another than the ends of the arms connected to the handle; and
    a length of thread coupled to and extending between distal ends of the arms,
    wherein the handle walls form a portion in a bottom surface of the handle which is configured to be received by the cavity in the top surface of a substantially identical, oral care device so that the devices are nestable when a plurality of the oral care devices are stacked one upon the other.

* * * * *